United States Patent [19]

Masaki et al.

[11] 4,133,831

[45] Jan. 9, 1979

[54] PROCESS FOR CATALYTICALLY PRODUCING PHOSGENE

[75] Inventors: Mitsuo Masaki, Chiba; Susumu Fuzimura, Ichihara, both of Japan

[73] Assignee: UBE Industries, Ltd., Ube, Japan

[21] Appl. No.: 885,605

[22] Filed: Mar. 13, 1978

[30] Foreign Application Priority Data

Mar. 18, 1977 [JP] Japan ................................. 52-29305

[51] Int. Cl.$^2$ ............................................... C07F 9/02
[52] U.S. Cl. ................................................. 260/544 K
[58] Field of Search ..................................... 260/544 K

[56] References Cited

U.S. PATENT DOCUMENTS

| | | | |
|---|---|---|---|
| 1,457,493 | 6/1923 | Bradner | 260/544 K |
| 2,847,470 | 8/1958 | Douthitt | 260/544 K |
| 3,515,752 | 6/1970 | Bauer | 260/544 K |
| 3,996,273 | 12/1976 | Daumas | 260/544 K |

*Primary Examiner*—Gerald A. Schwartz
*Attorney, Agent, or Firm*—Miller & Prestia

[57] ABSTRACT

Disclosed is a process for catalytically producing phosgene in a high yield in a solvent. In this process, carbon monoxide gas is brought into contact with a solution containing chlorine and with a catalyst consisting of at least one phosphine chloride compound, so as to cause the carbon monoxide to react with the chlorine. The phosphine chloride catalyst compound can be selected from substituted and unsubstituted trialkylphosphine dichlorides, substituted and unsubstituted tetraalkyldiphosphine tetrachlorides, substituted and unsubstituted alkylphosphorane dichlorides, and substituted and unsubstituted alkylene-bis(alkylphosphine) tetrachlorides.

25 Claims, No Drawings

PROCESS FOR CATALYTICALLY PRODUCING PHOSGENE

The present invention relates to a process for producing phosgene. More particularly, the present invention relates to a process for catalytically producing phosgene in a solvent.

Phosgene is useful as a material for producing isocyanates carbonates and intermediates of various organic compounds, for example, agricultural chemicals and medicines and as a chlorinating agent.

It is known that phosgene can be produced by a photochemical reaction of carbon monoxide with chlorine or by a catalytical reaction of carbon monoxide with chlorine in the presence of a catalyst consisting of activated carbon. The above-mentioned catalytic process in which the activated carbon is used as a catalyst is usually utilized for the industrial production of phosgene. In this process, a gas mixture of carbon monoxide and chlorine is fed into a reaction column and brought into contact with activated carbon contained in the reaction column. The catalytic reaction of carbon monoxide with chlorine is carried out at a temperature of from 60° to 150° C. under a pressure of 10 atmospheres or less. This process has the following disadvantages.

1. Since the reaction of carbon monoxide with chlorine is an exothermic reaction, the temperature of the reaction mixture increases with the lapse of the reaction time unless the reaction mixture is effectively cooled. The reaction rate varies in response to the temperature of the reaction mixture. Accordingly, in order to maintain the reaction at a constant rate, it is necessary to maintain the reaction temperature at a constant level. For this purpose, the peripheral surface of the reaction column is usually cooled so as to maintain a uniform distribution of temperature inside the reaction column. However, this cooling of the peripheral surface of the reaction column cannot completely prevent the inside space of the reaction column from local overheating. In order to increase uniformity in the cooling efficiency of the reaction column without decreasing the production of phosgene, a large number of thin, long reaction columns should be used. The use of a large number of reaction columns causes the reaction apparatus to be highly complex and large in scale.

2. In the above-mentioned process, phosgene is obtained in the state of a gas mixture containing non-reacted carbon monoxide and chlorine in addition to phosgene. Phosgene is isolated from the gas mixture by means of liquefaction. For this purpose, a separate apparatus for liquefying phosgene should be added to the reaction apparatus.

3. A high concentration of phosgene in the gas mixture cannot be obtained during the period from when the reaction is started to when the reaction attains a stationary state. That is, during the above-mentioned period, the resultant gas mixture contains a large amount of non-reacted carbon monoxide and chlorine.

4. When the reaction process is terminated, it is difficult to effectively utilize the phosgene-containing gas remaining in the reaction column.

5. As phosgene is deadly poisonous, it is therefore very dangerous to transport the phosgene-containing gas. In many developed countries, the transportation of poisonous materials is controlled by very strict laws.

6. Since the used activated carbon catalyst contains the deadly poisonous phosgene, the operation for recovering and reactivating the used activated carbon is dangerous.

7. The gas product contains certain amounts of non-reacted chlorine and carbon monoxide. Therefore, in order to obtain phosgene with a high degree of purity, it is necessary to refine the deadly poisonous gas product.

Under these circumstances, it is desirable to provide a convenient method for producing phosgene in a simple apparatus without the above-mentioned disadvantages.

An object of the present invention is to provide a process for catalytically producing phosgene in a uniform condition.

Another object of the present invention is to provide a process for catalytically producing phosgene, in which process the resultant phosgene can be easily isolated from the reaction mixture.

A further object of the present invention is to provide a process for catalytically producing phosgene in a relatively simple apparatus.

Another object of the present invention is to provide a process for catalytically producing phosgene with a high yield.

Still another object of the present invention is to provide a process for producing phosgene in a solvent, the resultant phosgene being completely free from molecular chlorine; thus, it is unnecessary to refine the phosgene by liquefaction.

The objects mentioned above can be attained by utilizing the process of the present invention, which comprises reacting carbon monoxide with chlorine in a solvent in the presence of a catalyst consisting of at least one phosphine chloride compound, and recovering the solution containing the resultant phosgene in the solvent.

The phosphine chloride compound which is usable as a catalyst for the process of the invention may be selected from the group consisting of the compounds of the formulae (1), (2), (3) and (4):

(1),

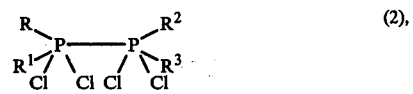
(2),

(3), and

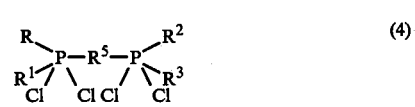
(4)

in which formulae R, $R^1$, $R^2$, and $R^3$ respectively represent, independently from each other, a substituted or unsubstituted alkyl group having 1 through 18 carbon atoms or a substituted or unsubstituted cycloalkyl group having 5 through 10 carbon atoms; $R^4$ represents a substituted or unsubstituted alkylene group having 4 through 6 carbon atoms; and $R_5$ represents an alkylene group having 1 through 6 carbon atoms or $-(CH_2CH_2O)_n CH_2CH_2-$ wherein n represents an integer of 1, 2 or 3.

In the compounds of the formulae (1), (2), (3) and (4), any one of the groups R, $R^1$, $R^2$ and $R^3$ may have at least one substituent selected from the group consisting of chlorine and fluorine atoms, alkoxyl groups having 1 to 6 carbon atoms and a cyano group, and $R^4$ may have at least one substituent selected from the group consisting of chlorine and fluorine atoms and alkyl groups having 1 through 6 carbon atoms. The phosphine chloride compound of the formula (1) may be selected from, for example, the group consisting of trimethylphosphine dichloride, triethylphosphine dichloride, tripropylphosphine dichloride, tributylphosphine dichloride, tripentylphosphine dichloride, trihexylphosphine dichloride, triheptylphosphine dichloride, trioctylphosphine dichloride, methylethylbutylphosphine dichloride, tricyclohexylphosphine dichloride, tris(2-cyanoethyl)phosphine dichloride, tris(trifluoromethyl)phosphine dichloride, tris(2-fluoroethyl)phosphine dichloride and tris(2-methoxyethyl)phosphine dichloride. The phosphine chloride compound of the formula (2) may be selected from, for example, the group consisting of tetramethyldiphosphine tetrachloride, tetraethyldiphosphine tetrachloride, 1,2-diethyl-1,2-dimethyldiphosphine tetrachloride, 1,2-dimethyl-1,2-bis(trifluoromethyl)diphosphine tetrachloride, tetrapropyldiphosphine tetrachloride, tetrabutyldiphosphine tetrachloride, tetracyclohexyldiphosphine tetrachloride, tetrakis(trifluoromethyl)diphosphine tetrachloride and tetrapentyldiphospine tetrachloride. The phosphine chloride compound of the formula (3) may be selected from, for example, the group consisting of 1-methylphosphorane dichloride, 1-ethyl-3-methylphosphorane dichloride and 1-butyl-3-hexylphosphorane dichloride. The phosphine chloride compound of the formula (4) may be selected from, for example, the group consisting of ethylene-bis(diethylphosphine) tetrachloride, ethylene-bis[bis(trifluoromethyl)phosphine] tetrachloride, trimethylene-bis(dibutylphosphine)tetrachloride, pentamethylene-bis(dicyclohexylphosphine)tetrachloride, [ethylene-bis(oxyethylene)]bis(dibutylphosphine)tetrachloride, 1,1'-ethylene-bis(phosphorane)tetrachloride and 1-(diethylphosphinoethyl)phosphorane tetrachloride.

The solvent which is usable for the process of the present invention is not restricted to a special group of liquid compounds as long as the liquid compound can dissolve therein chlorine, the above-mentioned phosphine chloride compound catalyst and phosgene. Furthermore, the solvent should not be reactive to any of the chlorine, carbon monoxide, phosgene and catalyst under the conditions under which the process of the present invention is carried out. For example, the solvent may be selected from the group consisting of tetrachloromethane, chloroform, tetrachloroethane, 1,1,2-trichloro-1,2,2-trifluoroethane, and mixtures of two or more of the above-mentioned compounds. Non-halogenated hydrocarbon compounds, for example, benzene, hexane, heptane and octane, are not suitable as the solvent for the process of the present invention, because the non-halogenated hydrocarbon compounds are reactive to chlorine. However, the non-halogenated hydrocarbons may be chlorinated with chlorine in the reaction apparatus of the process of the present invention to provide a solvent suitable for the process of the present invention, before the start of or during the catalytic reaction of carbon monoxide with chlorine.

In the case where the reaction of the process of the present invention is carried out in a darkroom condition, the non-halogenated hydrocarbons can be used as a solvent, because the non-halogenated hydrocarbons are not photochemically chlorinated in the dark.

In the process of the present invention, the phosphine chloride compound and chlorine are dissolved in the solvent, and carbon monoxide gas is brought into contact with the above-prepared solution.

The amount of catalyst in the solution is not limited to a special level. However, it is preferable that the amount of catalyst in the solution be in a range of from 0.1 to 100% based on the molar amount of either the carbon monoxide or the chlorine, whichever has the not larger molar amount. An amount of catalyst which is less than 0.1% sometimes results in an excessively low reaction rate of carbon monoxide with chlorine. The low reaction velocity will in turn cause the reaction time necessary for completing the reaction to be very long. An amount of catalyst which is more than 100% will not increase the reaction rate, which in turn disadvantageously increases the cost of the process.

The method for dissolving the chlorine in the solvent is not limited to any special method. Usually, any desired amount of liquid chlorine can be dissolved in the solvent.

In the process of the present invention, equal molar amounts of chlorine and carbon monoxide are allowed to react each other to produce a molar amount of phosgene which is equal to that of chlorine. Accordingly, in order to completely exhaust the chlorine contained in the solution, it is preferable that a molar amount of carbon monoxide which is at least the same as that of chlorine be brought into contact with the solution. It is more preferable to use carbon monoxide in a molar amount which exceeds that of the chlorine. An excessive amount of carbon monoxide is effective for shortening the time necessary for completing the reaction and for completely exhausting the chlorine in the solution. In this case, the resultant phosgene solution contains no chlorine. Accordingly, it is easy to obtain a very pure phosgene from the solution.

In the process of the present invention, carbon monoxide is usually used in a gaseous state.

The pressure of the carbon monoxide gas when it is brought into contact with the solution containing the catalyst and chlorine, is not limited to a special level. However, a preferable pressure of the carbon monoxide gas is one not exceeding 150 kg/cm², more preferably, one which is from atmospheric pressure to 150 kg/cm², still more preferably, from 5 to 100 kg/cm². A pressure lower than atmospheric pressure sometimes causes the rate of the reaction between carbon monoxide with chlorine to be excessively low. Also, a pressure higher than 150 kg/cm² will produce no advantageous reaction rate.

The temperature of the reaction system at which carbon monoxide reacts with chlorine is not limited to a special level. However, a preferable reaction temperature is one not exceeding 200° C., more preferably, one within a range of from 0° to 200° C., or still more preferably, from 10° to 150° C. A reaction temperature lower than 0° C. sometimes results in an excessively low reaction rate. Also, a reaction temperature higher than 200° C. will cause the resultant phosgene to be thermally decomposed and, therefore, to have a decreased yield.

The method for bringing the carbon monoxide into contact with the chlorine-containing solution is not limited to a special method, as long as the method is effective for causing the carbon monoxide to be in contact with the chlorine. For example, a solution of the catalyst and chlorine is shaken in a closed vessel such as an autoclave, which is filled with carbon monoxide gas.

In the process of the present invention, the phosphine chloride compound catalyst is dissolved in a solvent. The phosphine chloride compound can be prepared by reacting chlorine with a phosphine compound corresponding to the phosphine chloride compound. Accordingly, before the start of or at the first stage of the process reaction, the phosphine chloride compound catalyst may be prepared in the solvent by reacting chlorine with a precursory catalyst consisting of a phosphine compound corresponding to the catalytic phosphine chloride compound. The precursory catalytic phosphine compound may be selected from the group consisting of the compounds of the formulae (5), (6), (7) and (8):

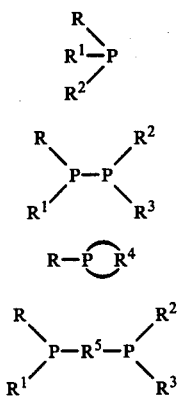

wherein R, $R^1$, $R^2$, $R^3$, $R^4$ and $R^5$ are respectively the same as those defined hereinbefore.

The phosphine compound of the formula (5) may be selected from, for example, the group consisting of trimethyl phosphine, triethyl phosphine, tripropyl phosphine, tributyl phosphine, tripentyl phosphine, trihexyl phosphine, triheptyl phosphine, trioctyl phosphine, methylethylbutyl phosphine, tricyclohexyl phosphine, tris(2-cyanoethyl)phosphine, tris(trifluoromethyl)phosphine, tris(2-fluoroethyl)phosphine and tris(2-methoxyethyl)phosphine.

The phosphine compound of the formula (6) may be selected from, for example, the group consisting of tetramethyl diphosphine, tetraethyl diphosphine, 1,2-diethyl-1,2-dimethyl diphosphine, 1,2-dimethyl-1,2-bis(trifluoromethyl)diphosphine, tetrapropyl diphosphine, tetrabutyl diphosphine, tetracyclohexyl diphosphine, tetrakis(trifluoromethyl)diphosphine and tetrapentyl diphosphine.

The phosphine compound of the formula (7) may be selected from, for example, the group consisting of 1-methyl phosphorane, 1-ethyl-3-methyl phosphorane and 1-butyl-3-hexyl phosphorane.

The phosphine compound of the formula (8) may be selected from, for example, the group consisting of ethylene-bis(diethylphosphine), ethylene-bis[bis(trifluoromethyl)phosphine], trimethylene-bis(dibutylphosphine,) pentamethylene-bis(dicyclohexylphosphine), [ethylene-bis(oxyethylene)]-bis(dibutyl phosphine), 1,1',-ethylene-bis(phosphorane) and 1-(diethylphosphinoethyl)phosphorane.

In the case where the precursory catalytic phosphine compound is converted in the solvent into a corresponding catalytic phosphine chloride compound at the first stage of the reaction process, it is necessary that the solution contains chlorine in an amount which is the sum of the amount necessary for converting the precursory catalytic compound into the corresponding to the catalytic compound and the amount necessary for producing a desired amount of phosgene.

In the case where the conversion of the precursory compound is effected before the start of the reaction process during the conversion stage, a predetermined molar amount of the precursory catalytic compound and at least a molar amount of chlorine which is the same as that of the precursory compound are dissolved in the solvent. After completion of the conversion, an additional amount of chlorine necessary for producing the desired amount of phosgene is dissolved in the solvent.

The phosphine chloride compound which is usable as a catalyst for the process of the present invention can also be prepared by reacting chloride and carbon monoxide with a phosphine oxide compound corresponding to the phosphine chloride compound. Accordingly, the phosphine chloride compound may be prepared in the solvent by reacting chlorine and carbon monoxide with a precursory catalyst consisting of a phosphine oxide compound corresponding to the phosphine chloride compound, before the start of or at the first stage of the process reaction.

The precursory catalytic phosphine oxide compound may be selected from the group consisting of the compounds of the formulae (9), (10), (11) and (12):

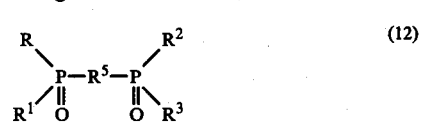

wherein R, $R^1$, $R^2$, $R^3$, $R^4$ and $R^5$ are respectively the same as those defined hereinbefore.

The phosphine oxide compound of the formula (9) may be selected from, for example, the group consisting of trimethyl phosphine oxide, triethylphosphine oxide, tripropyl phosphine oxide, tributyl phosphine oxide, trioctyl phosphine oxide, tripentylphosphine oxide, trihexylphosphine oxide, triheptylphosphine oxide, methylethylbutylphosphine oxide tricyclohexylphosphine oxide, tris(2-cyanoethyl)phosphine oxide, tris(trifluoromethyl)phosphine oxide, tris(2-fluoroethyl)phosphine oxide and tris(2-methoxyethyl)phosphine oxide.

The phosphine oxide compound of the formula (10) may be selected from, for example, the group consisting of tetramethyldiphosphine dioxide, tetraethyldiphosphine dioxide, 1,2-diethyl-1,2-dimethyldiphosphine dioxide, 1,2-dimethyl-1,2-bis(trifluoromethyl)diphosphine dioxide, tetrapropyldiphosphine dioxide, tetrabutyldiphosphine dioxide, tetracyclohexyldiphosphine dioxide, tetrakis(trifluoromethyl)diphosphine dioxide and tetrapentyldiphosphine dioxide.

The phosphine oxide compound of the formula (11) may be selected from, for example, the group consisting of 1-methylphosphorane oxide, 1-ethyl-3-methylphosphorane oxide and 1-butyl-3-hexylphosphorane oxide.

The phosphine oxide compound of the formula (12) may be selected from, for example, the group consisting of ethylene-bis(diethylphosphine)dioxide, ethylene-bis[bis(trifluoromethyl)phosphine]dioxide, trimethylene-bis(dibutylphosphine)dioxide, pentamethylene-bis(dicyclohexylphosphine)dioxide, [ethylene-bis(oxyethylene)]-bis(dibutylphosphine)dioxide, 1,1'-ethylene-bis(phosphorane)dioxide and 1-(diethylphosphinoethyl)phosphorane dioxide.

In the case where the required amount of the catalytic compound is prepared in the solvent by reacting chlorine and carbon monoxide with a precursory catalytic phosphine oxide compound during the first stage of the reaction process, it is necessary that the carbon monoxide and the chlorine be used in an amount which is at least the sum of the amount necessary for converting the precursory catalytic compound to the corresponding catalytic compound and the amount necessary for producing the desired amount of phosgene, respectively.

In the case where the conversion of the precursory catalytic phosphine oxide compound is effected before the start of the reaction process, a predetermined amount of the precursory catalytic compound and an amount of chlorine necessary for completely converting the precursory catalytic compound are dissolved in the solvent. The solution is then brought into contact with an amount of carbon monoxide gas necessary for completely converting the precursory catalytic compound. After the conversion is completed, an additional amount of chlorine necessary for producing the desired amount of phosgene is dissolved in the solution containing the catalyst and the resultant solution is brought into contact with an amount of carbon monoxide gas necessary for producing the desired amount of phosgene.

The phosphine chloride compounds which can be used in the present invention are generally very hygroscopic. Due to this property, these compounds will decompose if brought into contact with water. Accordingly, it is difficult for the phosphine chloride compounds to be stored over a long period of time or to be handled in an atmosphere containing moisture, without decomposition occurring thereto. Therefore, the above-mentioned conversion of the precursory catalytic compounds to the corresponding catalytic compounds in the solvent used for the reaction process is effective for preventing occurrences of the above-mentioned disadvantages of the catalytic compounds.

The period of time in which the reaction of carbon monoxide with chlorine is completed varies in accordance with the method for bringing the chlorine and catalyst-containing solution into contact with the carbon monoxide, the scale of the reaction apparatus, the reaction temperature, the reaction pressure and the type and amount of the catalytic compound used. However, the reaction process of the present invention can usually be completed within a relatively short time, for example, from 10 minutes to 6 hours.

When the reaction process is completed, the solution containing the resultant phosgene in the solvent is recovered. The solution should preferably be free from chlorine.

This solution may be utilized in situ as a source for supplying phosgene or as a phosgene-containing solution. The resultant phosgene can be isolated from the solution. The method for isolating the resultant phosgene from the solution is not restricted to any special method as long as the isolated phosgene has a desired degree of purity. Usually, the phosgene can be released in the state of a gas from the solution by reducing the pressure of the solution to a level lower than the reaction pressure under which the phosgene is produced and dissolved in the solution, or by elevating the temperature of the solution to a level higher than the reaction temperature at which the phosgene is produced and dissolved in the solution. The gaseous phosgene can be liquefied by cooling it to a temperature lower than its boiling point or by compression thereof.

After isolating the resultant phosgene from the solution, the remaining solution which contains the catalyst and the unisolated phosgene can be recycled for use in the reaction process. Accordingly, it is not always necessary to completely isolate the resultant phosgene from the solution.

In the process of the present invention, the reaction for producing phosgene is carried out in the solution containing chlorine and the catalyst. Accordingly, the heat generated by the exothermic reaction of chlorine with carbon monoxide can be easily removed only by cooling the solution while stirring or shaking the solution so as to maintain the reaction temperature at a predetermined level.

The reaction of chlorine with carbon monoxide in the process of the present invention is a quantitative reaction and can be carried out rapidly. Therefore, by using the carbon monoxide in a molar amount which exceeds that of the chlorine used, the chlorine can be completely exhausted. Thus, the resultant phosgene solution is completely free from chlorine.

Since the solubility of the carbon monoxide in the solvent is very low, it is very easy to remove the carbon monoxide from the reaction system to obtain a phosgene solution substantially free from the carbon monoxide.

Furthermore, the phosgene can be isolated from the solution by utilizing a simple process, and the remaining solution which contains the catalyst can be recycled for use in the reaction process. Therefore, the process of the present invention is very advantageous from an industrial viewpoint.

The following specific examples are for purposes of clarifying the process of the present invention. However, it should be understood that these are intended only to be examples of the present invention and not intended to limit the present invention in any way.

EXAMPLES 1 THROUGH 10

In Example 1, 0.41 g of tributylphosphine oxide, as a precursory catalytic compound, were dissolved in 50 ml of tetrachloromethane, and then 7.1 g of liquid chlorine were dissolved in the above-described solution. The solution was placed in a closed glass vessel having ventilating holes. The vessel was next placed and fixed in an autoclave. The autoclave was closed and then filled with 5140 Nml of carbon monoxide gas under a pressure of 10 kg/cm$^2$. The autoclave was shaken for 6 hours at a temperature of 20° C. to cause the chlorine to react with the carbon monoxide in the autoclave.

After the reaction process was completed, the glass vessel was removed from the autoclave. It was confirmed that the resultant solution contained phosgene and was free from chlorine. The yield of phosgene was determined as follows. Aniline and triethylamine respectively in a molar amount which is two times greater than that of the theoretical yield of phosgene were added to the resultant solution to convert the phosgene in the solution to diphenyl urea. The thus prepared diphenyl urea was separated from the solution by means of filtration followed by washing the filtration residue with water, and the amount of the diphenyl urea was determined. The yield of phosgene produced was calculated from the amount of the diphenyl urea. The results are shown in Table 1.

In each of Examples 2 through 10, procedures identical to those mentioned in Example 1 were carried out, except that, the amount of the liquid chlorine, the amount and pressure of the carbon monoxide, the type and amount of the solvent, the type and amount of the precursory catalytic compound, and the reaction temperature and time used are as shown in Table 1. The results are also shown in Table 1.

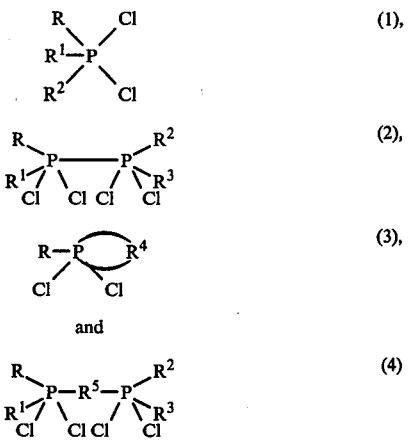

in which formulae R, $R^1$, $R^2$, and $R^3$ respectively represent, independently from each other, a substituted or Table I

| Ex. No. | Amount of liquid chlorine (g) | Carbon Monoxide Pressure | Solvent Type | Amount (ml) | Precursory catalytic compound Type | Amount (g) | Reaction temperature (° C) | Reaction time (hr.) | Yield of phosgene (%) |
|---|---|---|---|---|---|---|---|---|---|
| 1 | 7.1 | 10 | Tetrachloromethane | 50 | Tributylphosphine oxide | 0.41 | 20 | 6 | 91 |
| 2 | 2.5 | 10 | " | 20 | " | 0.34 | 40 | 1.5 | 94 |
| 3 | 2.3 | 10 | " | 20 | " | 0.33 | 60 | 1.0 | 78 |
| 4 | 7.4 | 30 | " | 50 | " | 0.40 | 20 | 1.5 | 89 |
| 5 | 7.9 | 60 | " | 50 | " | 0.42 | 20 | 0.5 | 98 |
| 6 | 7.5 | 60 | " | 50 | Tributylphosphine | 0.38 | 20 | 0.3 | 97 |
| 7 | 7.8 | 60 | " | 50 | Trioctylphosphine oxide | 0.38 | 20 | 0.7 | 88 |
| 8 | 6.7 | 60 | " | 50 | Triethylphosine oxide | 0.67 | 20 | 2 | 88 |
| 9 | 2.1 | 30 | 1,1,2,2-tetrachloroethane | 20 | Tributylphosphine oxide | 0.13 | 60 | 0.3 | 98 |
| 10 | 2.1 | 50 | " | 20 | " | 0.05 | 60 | 0.7 | 98 |

COMPARATIVE EXAMPLE 1

The same procedures as those mentioned in Example 1 were carried out, except that 0.15 g of activated carbon, as a catalyst, were suspended in 15 ml of tetrachloromethane, 1.1 g of liquid chlorine were dissolved in the suspension, carbon monoxide was charged into the autoclave under a pressure of 60 kg/cm², and the reaction was carried out at a temperature of 20° C. for 30 minutes.

The yield of phosgene was 25%.

COMPARATIVE EXAMPLE 2

The same procedures as those mentioned in Comparative Example 1 were carried out, except that, 0.20 g of activated carbon and 2.1 g of liquid chlorine were added to 22 ml of tetrachloromethane, and the reaction was carried out for 2 hours.

The yield of phosgene was 65%. What is claimed is:

1. A process for catalytically producing phosgene comprising, (a) reacting carbon monoxide with chlorine in a solvent in the presence of a catalyst consisting of at least the phosphine chloride compound selected from the group consisting of compounds of the formulae (1), (2), (3), and (4):

unsubstituted alkyl group having 1 through 18 carbon atoms or a substituted or unsubstituted cycloalkyl group having 5 through 10 carbon atoms; $R^4$ represents a substituted or unsubstituted alkylene group having 4 through 6 carbon atoms; and $R^5$ represents an alkylene group having 1 through 6 carbon atoms or $+CH_2CH_2O)_{\overline{n}}CH_2CH_2$—wherein n represents an interger of 1, 2 or 3; when substituted, the groups R, $R^1$, $R^2$, and $R^3$, independently, comprise a substituent selected from the class consisting of chlorine and fluorine atoms, alkoxyl groups having 1 to 6 carbon atoms and a cyano group; and when substituted, the group $R^4$ comprises a substituent selected from the class consisting of chlorine and fluorine atoms and alkyl groups having 1 to 6 carbon atoms; and (b) recovering the solution containing the resultant phosgene in said solvent.

2. A process as claimed in claim 1, wherein said phosphine chloride compound of the formula (1) is selected from the group consisting of trimethylphosphine dichloride, triethylphosphine dichloride, tripropylphosphine dichloride, tributylphosphine dichloride, tripentylphosphine dichloride, trihexylphosphine dichloride, triheptylphosphine dichloride trioctylphosphine dichloride, methylethylbutylphosphine dichloride, tricyclohexylphosphine dichloride, tris(2-cyanoethyl)phosphine dichloride, tris(trifluoromethyl)phosphine dichloride, tris(2-fluoroethyl)phosphine dichloride and tris(2-methoxyethyl)phosphine dichloride.

3. A process as claimed in claim 1, wherein said phosphine chloride compound of the formula (2) is selected from the group consisting of tetramethyldiphosphine tetrachloride, tetraethyldiphosphine tetrachloride, 1,2-diethyl-1,2-dimethyldiphosphine tetrachloride, 1,2-dimethyl-1,2-bis(trifluoromethyl)diphosphine tetrachloride, tetrapropyldiphosphine tetrachloride, tetrabutyldiphosphine tetrachloride, tetracyclohexyldiphosphine tetrachloride, tetrakis(trifluoromethyl)diphosphine tetrachloride and tetrapentyldiphosphine tetrachloride.

4. A process as claimed in claim 1, wherein said phosphine chloride compound of the formula (3) is selected from the group consisting of 1-methylphosphorane dichloride, 1-ethyl-3-methylphosphorane dichloride and 1-butyl-3-hexylphosphorane dichloride.

5. A process as claimed in claim 1, wherein said phosphine chloride compound of the formula (4) is selected from the group consisting of ethylene-bis(diethylphosphine) tetrachloride, ethylene-bis[bis(trifluoromethyl)phosphine] tetrachloride, trimethylene-bis(dibutylphosphine)tetrachloride, pentamethylene-bis(dicyclohexylphosphine)tetrachloride, [ethylene-bis(oxyethylene)]-bis(dibutylphosphine)tetrachloride, 1,1'-ethylene-bis(phosphorane)tetrachloride and 1-(diethylphosphinoethyl)phosphorane tetrachloride.

6. A process as claimed in claim 1, wherein the amount of said catalyst in the reaction mixture is in a range of from 0.1 to 100% based on the molar amount of either the carbon monoxide or the chlorine, whichever has the not larger molar amount.

7. A process as claimed in claim 1, wherein said solvent is selected from the group consisting of tetrachloromethane, chloroform, tetrachloroethane, 1,1,2-trichloro-1,2,2-trifluoroethane, and mixtures of two or more of the above-mentioned compounds.

8. A process as claimed in claim 1, wherein said reaction is carried out at a temperature not exceeding 200° C.

9. A process as claimed in claim 1, wherein said carbon monoxide is fed in the state of a gas under a pressure not exceeding 150 kg/cm$^2$ into the reaction system.

10. A process as claimed in claim 1, wherein said chlorine is dissolved in said solvent.

11. A process as claimed in claim 1, wherein said phosphine chlorine compound is prepared in said solvent by reacting chlorine with a precursory catalyst consisting of a phosphine compound corresponding to said phosphine chloride compound.

12. A process as claimed in claim 11, wherein said precursory catalytic phosphine compound is selected from the group consisting of the compounds of the formulae (5), (6), (7) and (8):

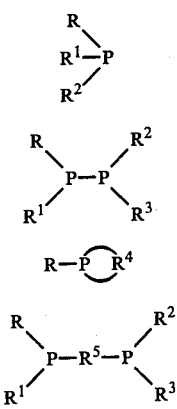

wherein R, R$^1$, R$^2$, R$^3$, R$^4$ and R$^5$ are respectively the same as those defined hereinbefore.

13. A process as claimed in claim 12, wherein said phosphine compound of the formula (5) is selected from the group consisting of trimethyl phosphine, triethyl phosphine, tripropyl phosphine, tributyl phosphine, tripentyl phosphine, trihexyl phosphine, triheptyl phosphine, trioctyl phosphine, methylethylbutyl phosphine, tricyclohexyl phosphine, tris(2-cyanoethyl)phosphine, tris(trifluoromethyl)phosphine, tris(2-fluoroethyl)phosphine and tris(2-methoxyethyl)phosphine.

14. A process as claimed in claim 12, wherein said phosphine compound of the formula (6) is selected from the group consisting of tetramethyl diphosphine, tetraethyl diphosphine, 1,2-diethyl-1,2-dimethyl diphosphine, 1,2-dimethyl-1,2-bis(trifluoromethyl)diphosphine, tetrapropyl diphosphine, tetrabutyl diphosphine, tetracyclohexyl diphosphine, tetrakis(trifluoromethyl)phosphine and tetrapentyl diphosphine.

15. A process as claimed in claim 12, wherein said phosphine compound of the formula (7) is selected from the group consisting of 1-methyl phosphorane, 1-ethyl-3-methyl phosphorane and 1-butyl-3-hexyl phosphorane.

16. A process as claimed in claim 12, wherein said phosphine compound of the formula (8) is selected from the group consisting of ethylene-bis(diethylphosphine), ethylene-bis[bis(trifluoromethyl)phosphine], trimethylene-bis(dibutylphosphine), pentamethylene-bis(dicyclohexylphosphine), [ethylene-bis(oxyethylene)]-bis(dibutyl phosphine), 1,1',-ethylene-bis(phosphorane) and 1-(diethylphosphinoethyl)phosphorane.

17. A process as claimed in claim 1, wherein said phosphine chloride compound is prepared in said solvent by reacting chlorine and carbon monoxide with a precursory catalyst consisting of a phosphine oxide compound corresponding to said phosphine chloride compound.

18. A process as claimed in claim 17, wherein said precursory catalytic phosphine oxide compound is selected from the group consisting of the compounds of the formulae (9), (10), (11) and (12):

wherein R, R$^1$, R$^2$, R$^3$, R$^4$ and R$^5$ are respectively the same as defined hereinbefore.

19. A process as claimed in claim 18, wherein said phosphine oxide compound of the formula (9) is selected from the group consisting of trimethyl phosphine oxide, triethylphosphine oxide, tripropyl phosphine oxide, tributylphosphine oxide, tripentylphosphine oxide, trihexylphosphine oxide, triheptylphosphine oxide, trioctyl phosphine oxide, methylethylbutylphosphine oxide, tricyclohexylphosphine oxide, tris(2-cyanoethyl)phosphine oxide, tris(trifluoromethyl)phosphine oxide, tris(2-fluoroethyl)phosphine oxide, and tris(2-methoxyethyl)phosphine oxide.

20. A process as claimed in claim 18, wherein said phosphine oxide compound of the formula (10) is selected from the group consisting of tetramethyldiphosphine dioxide, tetraethyldiphosphine dioxide, 1,2-diethyl-1,2-dimethyldiphosphine dioxide, 1,2-dimethyl-1,2-bis(trifluoromethyl)diphosphine dioxide, tetrapropyldiphosphine dioxide, tetrabutyl diphosphine dioxide, and tetracyclohexyl diphosphine dioxide, tetrakis(trifluoromethyl)disphosphine dioxide tetrapentyldiphosphine dioxide.

21. A process as claimed in claim 18, wherein said phosphine oxide compound of the formula (11) is selected from the group consisting of 1-methylphosphorane oxide, 1-ethyl-3-methylphosphorane oxide and 1-butyl-3-hexylphosphorane oxide.

22. A process as claimed in claim 18, wherein said phosphine oxide compound of the formula (12) is selected from the group consisting of ethylene-bis(diethylphosphine)dioxide, ethylene-bis[bis(trifluoromethyl)phosphine]dioxide, trimethylene-bis(dibutylphosphine)dioxide, pentamethylene-bis(dicyclohexylphosphine)dioxide, ethylene-bis(oxyethylene)bis(dibutylphosphine)dioxide, 1,1-ethylene-bis(phosphorane)dioxide and 1-(diethylphosphinoethyl)phosphorane dioxide.

23. A process as claimed in claim 1, wherein said resultant phosgene is isolated from said recovered solution.

24. A process as claimed in claim 23, wherein said phosgene is released from said solution by reducing the pressure of the solution to a level lower than the pressure under which said reaction process is carried out.

25. A process as claimed in claim 24, wherein said phosgene is released from said solution by elevating the temperature of the solution to a level higher than the temperature at which the reaction process is carried out.

* * * * *